(12) United States Patent
Park et al.

(10) Patent No.: US 12,171,661 B1
(45) Date of Patent: Dec. 24, 2024

(54) DEVICES FOR FATIGUE TESTING MEDICAL DEVICES AND SYSTEMS AND METHODS FOR USE

(71) Applicant: THE BOARD OF TRUSTEES OF THE LELAND STANFORD JUNIOR UNIVERSITY, Stanford, CA (US)

(72) Inventors: Matthew Park, Piedmont, CA (US); Annabel M. Imbrie-Moore, Stanford, CA (US); Yuanjia Zhu, Stanford, CA (US); Joseph Woo, Stanford, CA (US)

(73) Assignee: The Board of Trustees of the Leland Stanford, Jr. University, Stanford, CA (US)

( * ) Notice: Subject to any disclaimer, the term of this patent is extended or adjusted under 35 U.S.C. 154(b) by 282 days.

(21) Appl. No.: 17/551,114

(22) Filed: Dec. 14, 2021

Related U.S. Application Data (60) Provisional application No. 63/125,324, filed on Dec. 14, 2020.

(51) Int. Cl.
*A61F 2/24* (2006.01)
*G01N 3/34* (2006.01)

(52) U.S. Cl.
CPC .......... *A61F 2/2472* (2013.01); *A61F 2/2445* (2013.01); *G01N 3/34* (2013.01); *A61F 2240/008* (2013.01)

(58) Field of Classification Search
CPC ................ A61F 2/2472; A61F 2/2445; A61F 2240/008; G01N 3/34
See application file for complete search history.

(56) References Cited

U.S. PATENT DOCUMENTS 2,849,877 A * 9/1958 Burgett .................... G01N 3/32
                                                              73/808

FOREIGN PATENT DOCUMENTS

WO    WO-2020025755 A1 * 2/2020 ............. A61C 19/04

OTHER PUBLICATIONS

Armentia, M., Abasolo, M., Coria, I., Heras, I., Vallejo, J., Aguirrebeitia, J. (2019). Design of an innovative fatigue test bench for dental implants. In: Uhl, T. (eds) Advances in Mechanism and Machine Science. IFToMM WC 2019. Mechanisms and Machine Science, vol. 73. Springer, Cham. (Year: 2019).*

* cited by examiner

*Primary Examiner* — Eric S. McCall
*Assistant Examiner* — Timothy P Graves
(74) *Attorney, Agent, or Firm* — William A. English; Vista IP Law Group LLP (57) ABSTRACT

Devices and methods are provided for fatigue testing a medical device, e.g., an annuloplasty ring, using a cam rotatably mounted relative to a base and one or more sets of mounts on the base for securing opposite ends of the medical device. For example, each set of mounts may include a stationary mount on the base, a sliding mount on the base adjacent the cam, and a follower slidably mounted to the sliding mount that contacts the cam such that the follower reciprocates along a horizontal axis as the cam rotates about a vertical axis. The follower and stationary mount include connectors to secure opposite ends, respectively, of a medical device such that rotation of the cam causes the follower to reciprocate and apply tensile and/or compressive loads to fatigue test the medical device.

17 Claims, 6 Drawing Sheets

DEVICES FOR FATIGUE TESTING MEDICAL DEVICES AND SYSTEMS AND METHODS FOR USE

RELATED APPLICATION DATA

The present application claims benefit of provisional application Ser. No. 63/125,324, filed Dec. 14, 2020, the entire disclosure of which is expressly incorporated by reference herein.

TECHNICAL FIELD

The present application relates to devices for testing medical devices and, more particularly, to devices for performing fatigues tests on annuloplasty rings, and to systems and methods for using such testing devices.

BACKGROUND

Valvular heart disease is a common cause of morbidity and mortality globally and affects approximately 2.5% of the United States population. The most prevalent cause of valvular heart disease is mitral regurgitation. There are several causes of mitral regurgitation, including primary disease of the mitral valve apparatus (e.g., rupture of the chordae tendineae, failure of the leaflets, papillary muscle dysfunction, and infectious disease) and secondary regurgitation due to left ventricular enlargement. As the heart experiences MR, the left ventricle ("LV") dilates over time to compensate for reduced forward stroke volume. This enlargement of the LV leads to an increase in the annulus size, which further worsens MR. Thus, regardless of etiology, most patients with chronic MR exhibit some degree of mitral annular dilation and highly asymmetrically with the predominant dilation occurring across the posterior annulus.

Ring annuloplasty is a common surgical procedure for repairing MR. By using an annuloplasty ring to restore the pathophysiologically dilated annulus to a normal diameter, leaflet coaptation is improved and further annular dilation is prevented. Many annuloplasty ring variations exist, although there is little data on which has the most optimal geometry and material composition.

Generally, to test new surgical and/or other devices, companies and research institutions alike verify their efficacy using small or large animal models, which may increase cost and/or reduce statistical power (fewer n). Computer simulations may be used but may not accurately model actual device performance.

Therefore, new devices and methods that facilitate testing annuloplasty rings would be useful.

SUMMARY

The present application is directed to devices for testing medical devices and, more particularly, to devices for performing fatigues tests on annuloplasty rings or other medical devices that may be implanted within a subject's heart, such as annuloplasty rings for the mitral valve, and to systems and methods for using such testing devices.

In one example, a fatigue testing device is disclosed that may facilitate rapidly testing annuloplasty rings, e.g., to simulate twenty year performance and/or other durability parameters. Generally, the device transforms the rotary motion of a motor shaft to linear loading of an annuloplasty ring or other medical device using a rotary mechanical linkage or cam. For example, an ellipsoidal or irregularly shaped cam mechanism mounted on the motor shaft may rotate against a linearly constrained annuloplasty ring which may undergo loading at much faster rates than physiological conditions (e.g., up to 100-350 Hz), e.g., to simulate extended use of the ring. In an exemplary implementation, the ring is linearly constrained via two stainless steel rods that are mounted in a 3D-printed apparatus. Rotary motors may be less expensive than linear actuators, which may reduce costs, e.g., to test multiple devices simultaneously, and improve test results.

In accordance with another example, a device is provided for device for performing fatigue testing a device that includes a support platform; a cam rotatably mounted relative to a central region of the support platform such that the cam rotates about a first axis; and one or more sets of mounts on the support platform, each set of mounts comprising a first mount; a second mount adjacent the central region such that the first and second mounts are aligned along a second axis orthogonal to and intersecting the first axis; and a follower slidably mounted to the second mount such that a first end of the follower contacts the cam such that the follower reciprocates along the second axis as the cam rotates about the first axis, and wherein the follower and first mount are configured to secure first and second ends, respectively, of the device being tested such that rotation of the cam causes the follower to reciprocate and direct the first end of the device being tested away from and towards the second end.

In accordance with still another example, a device is provided for performing fatigue testing a medical device that includes a support platform comprising an upper surface, a vertical axis extending substantially perpendicular to the upper surface at a central region, and a set of mounts on the upper surface including a first mount on the upper surface, a second mount on the upper surface adjacent the central region such that the first and second mounts are aligned along a second axis orthogonal to and intersecting the first axis, and a follower slidably mounted to the second mount such that follower is slidable along the horizontal axis; and a cam rotatably mounted above the upper surface and aligned with the vertical axis such a first end of each follower contacts the cam and causes the follower to reciprocate along the horizontal axis as the cam rotates, wherein the follower and first mount are configured to secure first and second ends, respectively, of the device being tested such that rotation of the cam causes the follower to reciprocate and direct the first end of the device being tested away from and towards the second end.

In accordance with yet another example, a device is provided for performing fatigue testing a medical device that includes a support platform comprising an upper surface, a vertical axis extending substantially perpendicular to a central region of the upper surface, and one or more sets of mounts on the upper surface adjacent the central region, each set of mounts including a stationary mount on the upper surface and a sliding mount on the upper surface adjacent the central region such that the stationary and sliding mounts are aligned on a horizontal axis extending substantially perpendicular to the vertical axis; a motor adjacent the platform comprising a rotating axle aligned with the vertical axis at the central region; a cam mounted on the axle such that the cam rotates about the vertical axis above the upper surface as the axle rotates, the cam comprising a noncircular side surface that rotates around the vertical axis as the cam rotates, the side surface defining a major axis and a minor axis smaller than and orthogonal to the major axis; and a follower slidably mounted on each sliding mount comprising a first end that contacts the side surface such that the follower reciprocates along the horizontal axis as the cam rotates, wherein the follower and the stationary mount are configured to secure first and second ends, respectively, of a medical device such that rotation of the axle causes the follower to reciprocate and direct the first end of the medical device away from and towards the second end as the cam rotates.

In accordance with yet another example, a system is provided for performing fatigue testing of an annuloplasty ring comprising an elongate curved posterior segment and first and second curved lateral segments extending from opposite ends of the posterior segment. The system may include a support platform comprising an upper surface, a vertical axis extending substantially perpendicular to the upper surface at a central region, and one or more sets of mounts on the upper surface adjacent the central region, each set of mounts including a stationary mount on the upper surface and a sliding mount on the upper surface adjacent the central region such that the stationary and sliding mounts are aligned on a horizontal axis extending substantially perpendicular to the vertical axis; a motor adjacent the platform comprising a rotating axle aligned with the vertical axis at the central region; a cam mounted on the axle such that the cam rotates about the vertical axis above the upper surface as the axle rotates, the cam comprising a noncircular side surface that rotates around the vertical axis as the cam rotates, the side surface defining a major axis and a minor axis smaller than and orthogonal to the major axis; and a follower slidably mounted on each sliding mount comprising a first end that contacts the side surface such that the follower reciprocates along the horizontal axis as the cam rotates, wherein the follower and the stationary mount comprise first and second connectors for securing the first and second lateral segments, respectively, such that rotation of the axle causes the follower to reciprocate and direct the first and second lateral segments away from and towards one another along the horizontal axis, e.g., to perform rapid linear fatigue testing of the annuloplasty ring.

In accordance with another example, a method is provided for performing fatigue testing of a device, e.g., an annuloplasty ring or other medical device, that includes providing a support platform including a cam rotatably mounted relative to a central region of the support platform such that the cam rotates about a first axis; providing a device mount on the support platform including a first mount, a second mount adjacent the central region such that the first and second mounts are aligned along a second axis orthogonal to and intersecting the first axis, and a follower slidably mounted to the second mount such that a first end of the follower contacts the cam; connecting a first end of the device being tested to the first mount; connecting a second end of the device being tested to the follower; and rotating the cam to cause the follower to reciprocate the second end of the device along the second axis as the cam rotates.

In accordance with still another example, a method is provided for performing fatigue testing of a device, e.g., an annuloplasty ring or other medical device, that includes providing a support platform comprising an upper surface, a cam mounted above the upper surface and rotatable about a vertical axis extending substantially perpendicular to the upper surface, and one or more sets of mounts on the upper surface adjacent the central region, each set of mounts including a stationary mount on the upper surface and a sliding mount carrying a follower on the upper surface adjacent the cam such that the follower contacts the cam; connecting a first end of the medical device to the stationary mount; connecting a second end of the medical device to the follower; and rotating the cam to cause the follower to reciprocate and direct the first end of the medical device away from and towards the second end as the cam rotates.

In accordance with yet another example, a method is provided for performing fatigue testing of a device, e.g., an annuloplasty ring or other medical device, that includes a constrained linkage-based system, e.g., a two-bar linkage connected to a linearly constrained slider. These linkage systems may be actuated about any of the three spatial axes with the linear motion occurring in any axis. Such a mechanism may include a Scotch yoke, eccentric linkage, or other mechanism operatively coupling a flywheel to a piston, all of which generate a translation of rotary to linear motion. These systems may include one or more bearings and/or hinges at linkage joints.

In accordance with another example, a device is provided for performing fatigue testing a device that includes a support platform comprising an upper surface, a vertical axis, and one or more sets of mounts on the upper surface, each set of mounts including a stationary mount on the upper surface and a sliding mount on the upper surface adjacent the vertical axis; and a rotating device rotatably mounted above the upper surface and aligned with the vertical axis and operatively coupled to the sliding mount, wherein the sliding mount and the stationary mount are configured to secure first and second ends, respectively, of the device being tested such that rotation of the rotating device causes the sliding mount to reciprocate linearly and direct the first end of the device being tested away from and towards the second end.

It will be appreciated that the devices, systems, and methods herein may be particularly useful for performing rapid linear testing of cardiac devices, i.e., by translating the continuous rotation of the cam to linear motion acting on the device being tested, which may facilitate rapid, repeated, cyclical testing, e.g., simulating forces that the device may be subjected to within a beating heart, as well as other medical devices, such as prostheses or implants. However, the systems and methods herein may also be useful for performing such fatigue testing on other, e.g., non-medical devices that may be mounted to the fatigue testing device and subjected to reciprocating linear motion, such as springs, chairs, pistons, suspensions, switches, sports equipment, protective gear, and the like. Additionally, while the cam may be designed as ellipsoidal, any desired shape may be used depending on the target loading conditions for the device being tested. This is because any desired cyclic loading trajectory can generate a corresponding unique cam shape that matches that trajectory.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

DETAILED DESCRIPTION

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 1A:
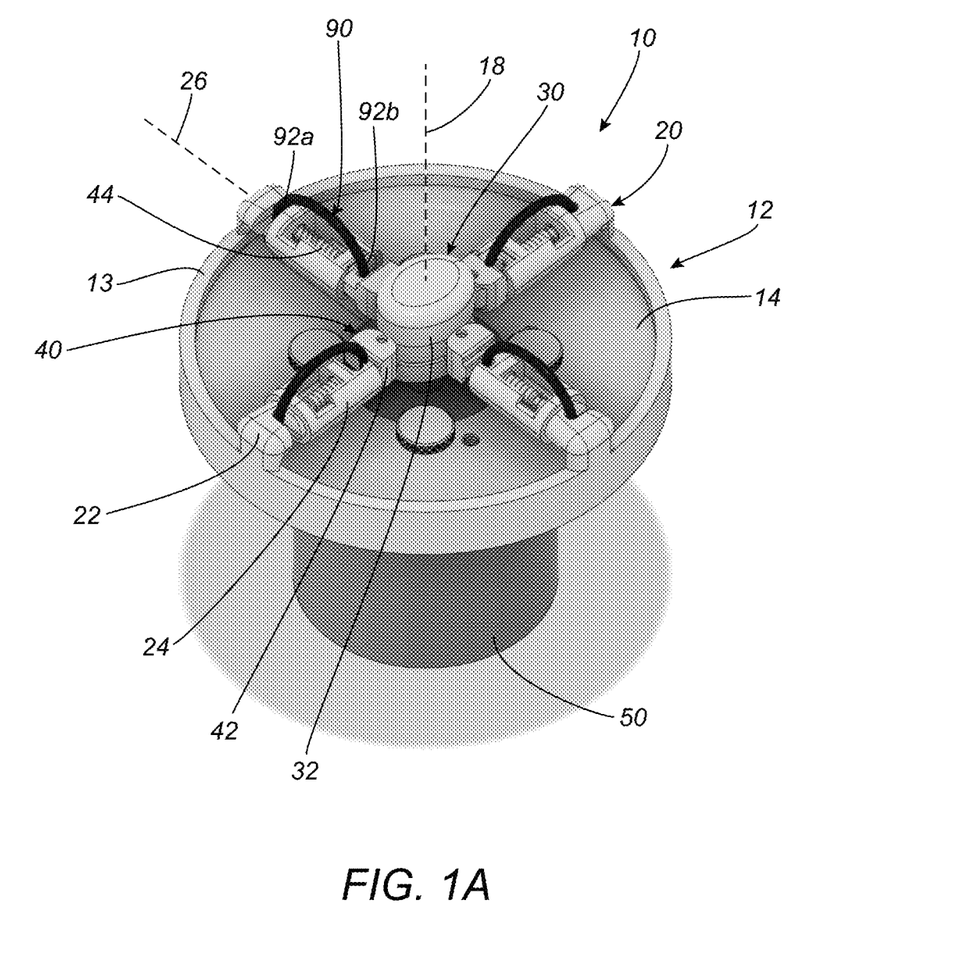
FIGS. 1A-1C show various views of an example of a fatigue testing device.
Figure 1B:
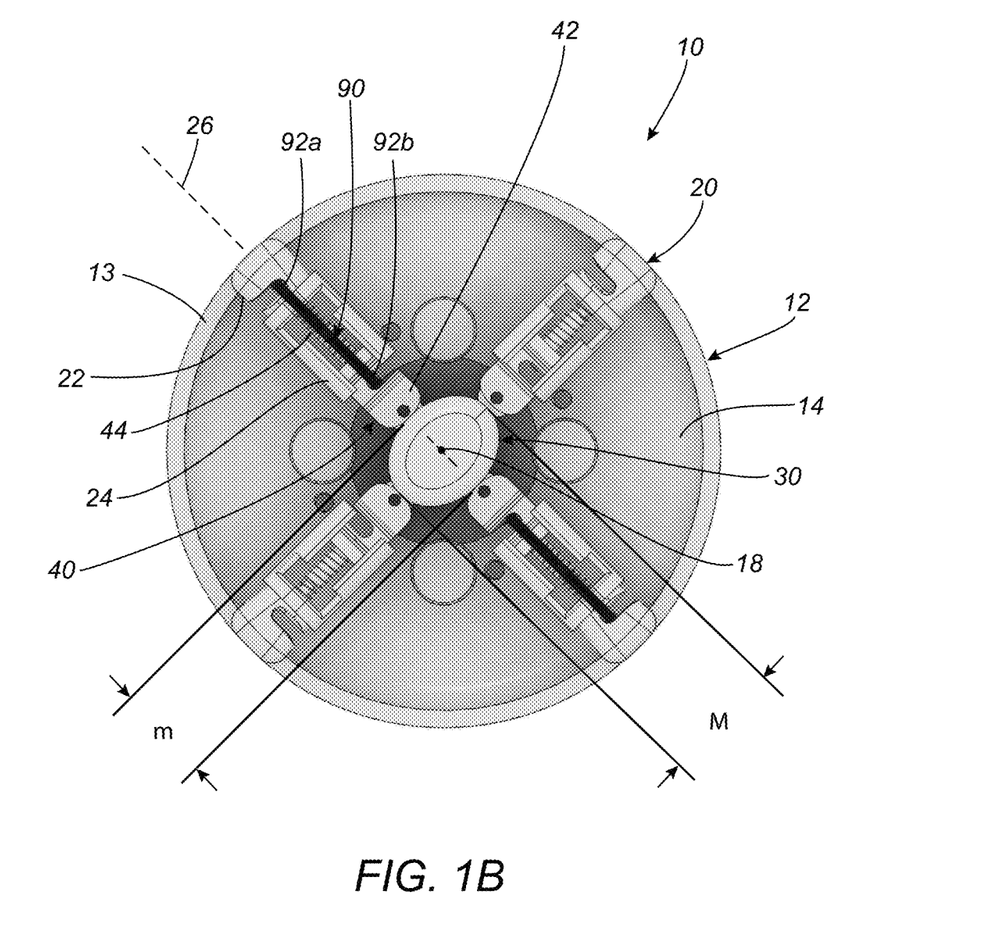
Figure 1C:
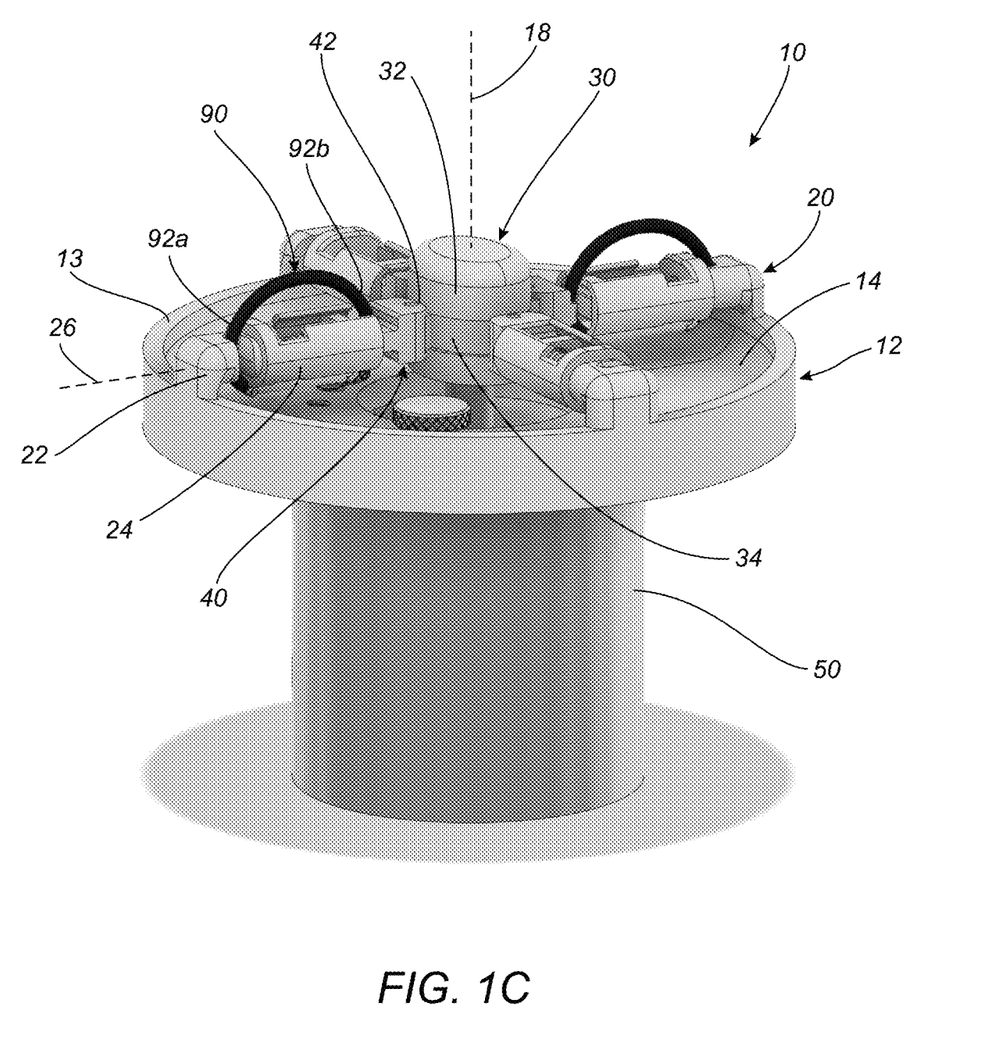

Turning to the drawings, FIGS. 1A-1C show an example of a device 10 for performing fatigue testing of a medical device, such as an annuloplasty ring 90. Generally, the device 10 includes a platform, base, or other support structure 12 including an upper surface or region 14 including an aperture 16 in a central region, thereby defining a vertical or central axis 18 extending substantially perpendicular to the upper surface 14.

One or more sets of mounts 20 may be provided on the upper surface 14 or otherwise fixed to the platform 12 adjacent the central aperture 16, e.g., a plurality of sets of mounts 20 arranged radially around the central aperture 16. For example, as shown in FIGS. 1A-1C, four sets of mounts 20 may be provided, e.g., for simultaneously testing four annuloplasty rings, although it will be appreciated that two, three, or other numbers of mounts may be accommodated depending on the size and spacing available on the platform 12. Alternatively, a testing device may be provided that includes only a single set of mounts on a platform or base for testing a single device, e.g., similar to the device 110 shown in FIGS. 2A and 2B and described further elsewhere herein.

Returning to FIGS. 1A-1C, each set of mounts 20 includes a first or stationary mount 22 fixed relative to the upper surface 14, e.g., adjacent an outer perimeter 13 of the platform 12, and a second or sliding mount 24 fixed relative to the upper surface 14 adjacent the central aperture 16 such that the stationary and sliding mounts 22, 24 are aligned on a horizontal or follower axis 26 orthogonal to the vertical axis 18, e.g., extending substantially perpendicular to and/or intersecting the vertical axis 18 such that the horizontal axis 26 extends substantially parallel to the upper surface 14.

A cam 30 may be rotatably mounted relative to the platform 12, e.g. aligned with the vertical axis 18 above the upper surface 14 and aperture 16, as shown. For example, a motor 50 may be mounted adjacent the platform 12, e.g., under or inside the platform 12, that includes a rotating axle (not shown) aligned with the vertical axis 18, e.g., extending through the aperture 16, and the cam 30 may be mounted on the axle, e.g., fixing the cam 30 from translating relative to the platform 12 while providing. Consequently, the cam 30 rotates about the vertical axis 18 above the upper surface 14 as the axle rotates.

The cam 30 includes a noncircular peripheral or outer side surface 32, e.g., having an elliptical or other cross-sectional shape, e.g., defining a major axis "M" and a minor axis "m" smaller than and orthogonal to the major axis, e.g., as best seen in FIG. 1B. The side surface 32 thus rotates around the vertical axis 18 as the cam 30 rotates. A follower 40 is slidably mounted to each sliding mount 24 that includes a first end 42 that contacts the side surface 32 such that the follower 40 reciprocates along the horizontal axis 26 as the cam 30 rotates. For example, the follower 40 may be slidable within a cavity or channel of the sliding mount 24, which may include a pair of side walls that allow the follower 40 to move along the horizontal axis 26 while preventing movement off the horizontal axis 26, as best seen in FIGS. 1A and 1B. Optionally, the follower 40 may be removable from the sliding mount 40, e.g., by separating the side walls or by removing the cam 30 to allow the follower 40 to slide out of the sliding mount 40, which may facilitate securing and/or removing a medical device 90 before and/or after testing, as described further elsewhere herein.

Optionally, the side surface 32 of the cam 30 may include a groove or other alignment feature 34, as can be seen in FIG. 1C, that slidably receives the first end 42 of the follower 40, e.g., to accommodate movement of the first end 42 back and forth along the horizontal axis 26 while preventing the first end 42 from moving vertically, i.e., along the vertical axis 18.

Optionally, the follower(s) 40 may be biased along the horizontal axis 26, e.g., towards an inward position closer to the vertical axis 18 and away from the outer perimeter 13 of the platform 12. For example, a spring mechanism 44 may be mounted within the sliding mount 24 to bias the follower 40 horizontally inwardly within the sliding mount 24, i.e., towards the vertical axis 18, but may accommodate the cam 30 pushing the follower 40 horizontally outwardly towards the stationary mount 22. In one example, the spring mechanism 44 includes a compression spring with a first end secured to the stationary mount 22 and a second end secured to the follower 40. The spring 44 may be compressed to maintain a continuous inward force against the follower 40, e.g., where the first end 42 is spaced from the vertical axis 18 by a distance less than half the major axis of the cam 30. Thus, the cam 30 may direct the follower(s) 40 to an outward position, i.e., closer to the stationary mount 22, when the major axis is aligned with the horizontal axis 26 as the cam 30 rotates and, given the bias, the follower 40 may automatically return towards the inward position when the minor axis is aligned with the horizontal axis 26 to maintain continuous contact with the cam 30.

The follower 40 and the stationary mount 22 are configured to secure a medical device 90 between them, e.g., securing opposite ends of the medical device 90, such that rotation of the cam 30 causes the follower 40 to reciprocate and direct the ends of the medical device 90 away from and towards one another. For example, the follower 40 and the stationary mount 22 may include connectors, e.g., a recess and/or one or more detents, fasteners, and the like (not shown), for removably connecting the opposite ends, respectively of the medical device 90 to the follower 40 and the stationary mount 22, as described further below. Optionally, the follower 40 may be removable from the sliding mount 24, e.g., to facilitate attaching an end of a medical device to the follower 40 before inserting the follower 40 into the sliding mount 24.

In the example shown in FIGS. 1A-1C, the medical device 90 may be an annuloplasty ring including an elongate curved posterior segment and first and second curved lateral segments extending from opposite ends of the posterior segment, e.g., defining an open "C" shape or an enclosed "D" shape similar to the annuloplasty rings disclosed in International application No. PCT/US2021/041803, filed Jul. 15, 2021, the entire disclosure of which is expressly incorporated by reference herein. As shown, a first lateral segment 92a is secured to the stationary mount 22 and a second opposite lateral segment 92b is secured to the follower 40. Consequently, rotation of the cam 30 causes the follower 40 to reciprocate and direct the second lateral segment 92b away from and towards the first lateral segment 92a (which remains stationary since it is secured to the stationary mount 22) along the horizontal axis 26, thereby alternately subjecting the annuloplasty ring 90 to tensile and/or compressive forces. It will be appreciated that a variety of medical devices may be similarly mounted to the follower 40 and stationary mount 22 to apply such alternating forces, e.g., to fatigue test the devices.

For example, during use, a first end 92a of a medical device 90 may be secured to one of the stationary mounts 22, and a second end 92b of the medical device 90 may be secured to the corresponding follower 40, which may be repeated to secure multiple devices 90 to the device 10 for testing, e.g., as shown in FIGS. 1A and 1B. For example, as shown, the first lateral segment 92a of each annuloplasty ring 90 may be received in a recess and/or otherwise secured to the stationary mount 22 and the second opposite lateral segment 92b may be received in a recess and/or otherwise secured to the follower 40, thereby linearly constraining the annuloplasty ring 90 along the horizontal axis 26. Thus, any desired number of annuloplasty rings 90, e.g., four as shown in FIG. 1A, may be mounted for testing simultaneously.

The motor may then be activated, thereby rotating the cam 30 to cause the follower(s) 40 to reciprocate horizontally and direct the second lateral segment 92b away from and towards the first lateral segment 92a as the cam 30 rotates to apply cyclical loads to the annuloplasty ring(s) 90. The motor may be activated for a desired time period, e.g., to simulate a target life for the annuloplasty ring 90(s), or until failure.

In one example, the axle and cam 30 may be rotated at a frequency, e.g., between about 8.3-25 Hertz (500-1500 rpm), such that the annuloplasty ring(s) 90 experience cycling speeds approximately fourteen to forty three (14-43) times faster than a resting heart rate of seventy beats per minute (70 bpm). In another example, the cam 30 may rotated at a frequency between about 100-350 Hertz, which may allow rapid fatigue testing of the annuloplasty ring(s) 90, e.g., allowing the equivalent of about twenty years of testing to be performed in a several days or months, e.g., about three months at three thousand rotations per minute (3000 rpm). Consequently, fatigue testing times may be reduced by up to fifty to one hundred fifty (50-150) times, e.g., compared to cycles similar to normal heart beats.

Figure 2A:
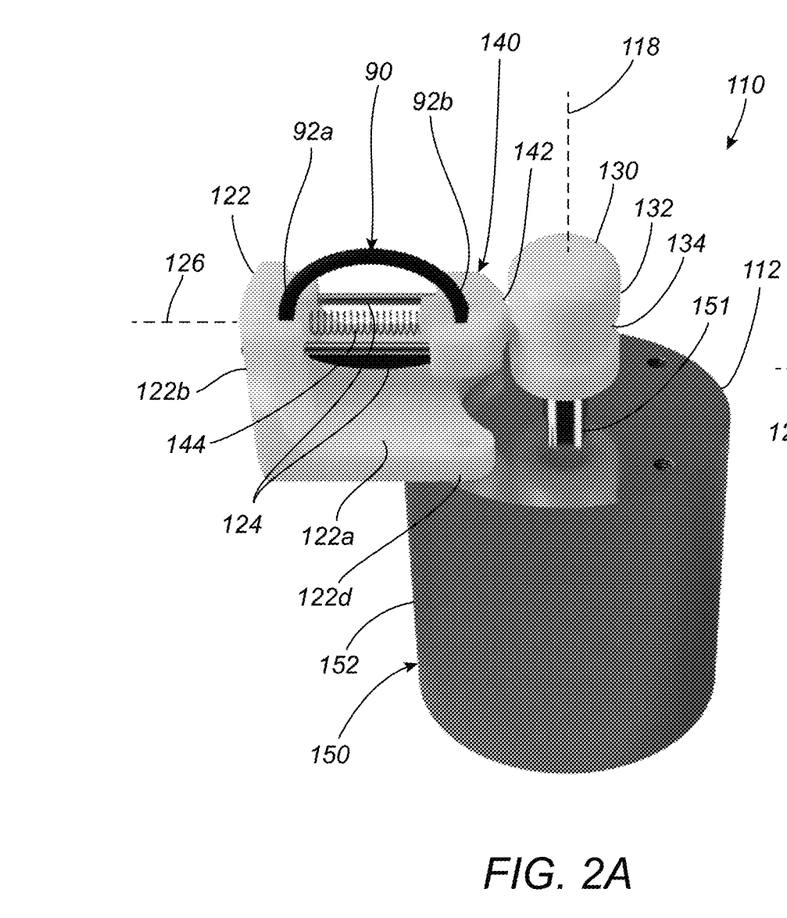
FIGS. 2A and 2B show various views of another example of a fatigue testing device.
Figure 2B:
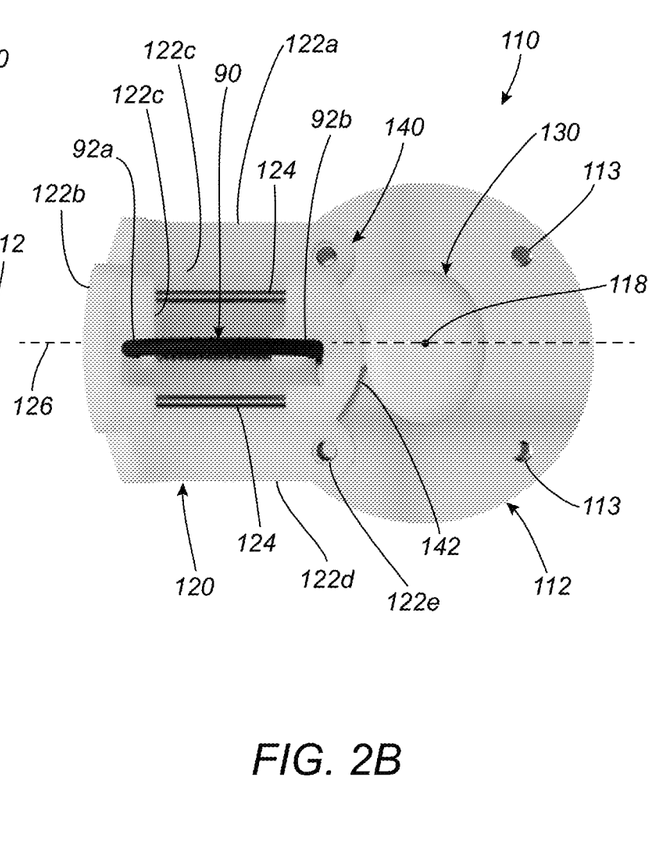

Turning to FIGS. 2A and 2B, another example of a fatigue testing device 110 is shown that includes a cam 130 mounted on an axle 151 of a motor 150 such that cam 130 may rotate about vertical axis 118. In this example, the motor 150 is contained with a housing 152 having an upper surface 112 to which one or more device mounts 120 may be secured. For example, as shown, the upper surface 112 may include one or more pairs of mounting holes 113 arranged around the cam 130 that may be used to secured each device mount 120. For example, as shown, the upper surface 112 includes two pairs of holes 113 on opposite sides of the cam 130, allowing two device mounts 120 to be secured to the housing 152 to test two devices 90 simultaneously (although only one is shown). Alternatively, it will be appreciated that the upper surface 112 may include one two, three, or more sets of mounting holes, depending on the size and spacing available on the housing 152.

Generally, similar to the device 10 each device mount 120 generally includes a first or stationary mount 122 that may be fixed relative to the upper surface 112, a second or sliding mount 124 fixed relative to the upper surface 112, and a follower 140 slidable mounted to the sliding mount 124 such that the followed 140 is movable along a horizontal axis 126 With the device mount 120 secured to the upper surface 112, a first end 142 of the follower 140 slidably contacts the side surface 132 of the cam 130, e.g., such that rotation of the cam 130 causes the follower 140 to reciprocate, also similar to the device 10.

However, in this example, the stationary mount 122 includes an elongate base 122a including an outer end 122b including one or more connectors 122c for securing a device, e.g., first end 92a of annuloplasty ring 90, and an inner end 122d including a pair of mounting holes 122e corresponding to the pair of holes 113 on the upper surface 112. For example, a bolt or other fastener (not shown) may be received in each of the holes 122e, 113 to secure the base 122a of the stationary mount 122 to the upper surface 112 and, consequently, relative to the cam 130. It will be appreciated that other connectors (not shown) may be used to removably or permanently mount the stationary mount 122 to the upper surface 112 such that the device mount 120 is secured relative to the cam 130.

In addition, in this example, the sliding mount 124 includes a pair of guide shafts extending from the hub 122b of the stationary mount 122 inwardly towards the cam 130 substantially parallel to the horizontal axis 126. For example, each guide shaft 124 may include a substantially rigid tube or rod including a first end permanently attached to the hub 122b, e.g., using one or more of integral molding or casting, bonding with adhesive, fusing, one or more connectors, and the like, and an inner end located adjacent, e.g., above, the inner end 122d.

The follower 140 may include a recess, channel, or hole sized to slidably receive each of the guide shafts 124 such that the follower 140 is free to slide parallel to the horizontal axis 126. Similar to the device 10, the follower 140 may be biased inwardly, e.g., by a compression spring 144 or other biasing mechanism, e.g., secured between the hub 122b and the follower 140 parallel to the horizontal axis 126. Optionally, the guide shafts 124 and/or follower 140 may include cooperating features that prevent the follower 140 from sliding off the inner ends of the guide shafts 124, e.g., before mounting the device mount 130 to the upper surface 112.

The device 110 may be used similar to the device 10, e.g., by securing a first end 92a of the annuloplasty ring 90 to the hub 122b of the stationary mount 122 and a second end 92b to the follower 140, e.g., using one or more cooperating connectors, and the like. In one method, the annuloplasty ring 90 may be secured to the hub 122b and follower 140 before the device mount 120 is secured to the upper surface 112, and then the assembly device mount 120 with the annuloplasty ring 90 may be secured to the upper surface 112. Alternatively, the annuloplasty ring 90 may be mounted to the device mount 120 after the inner end 122d is secured to the upper surface 112 (or in the alternative where the device mount 120 is not removable from the housing 152).

Figure 3A:
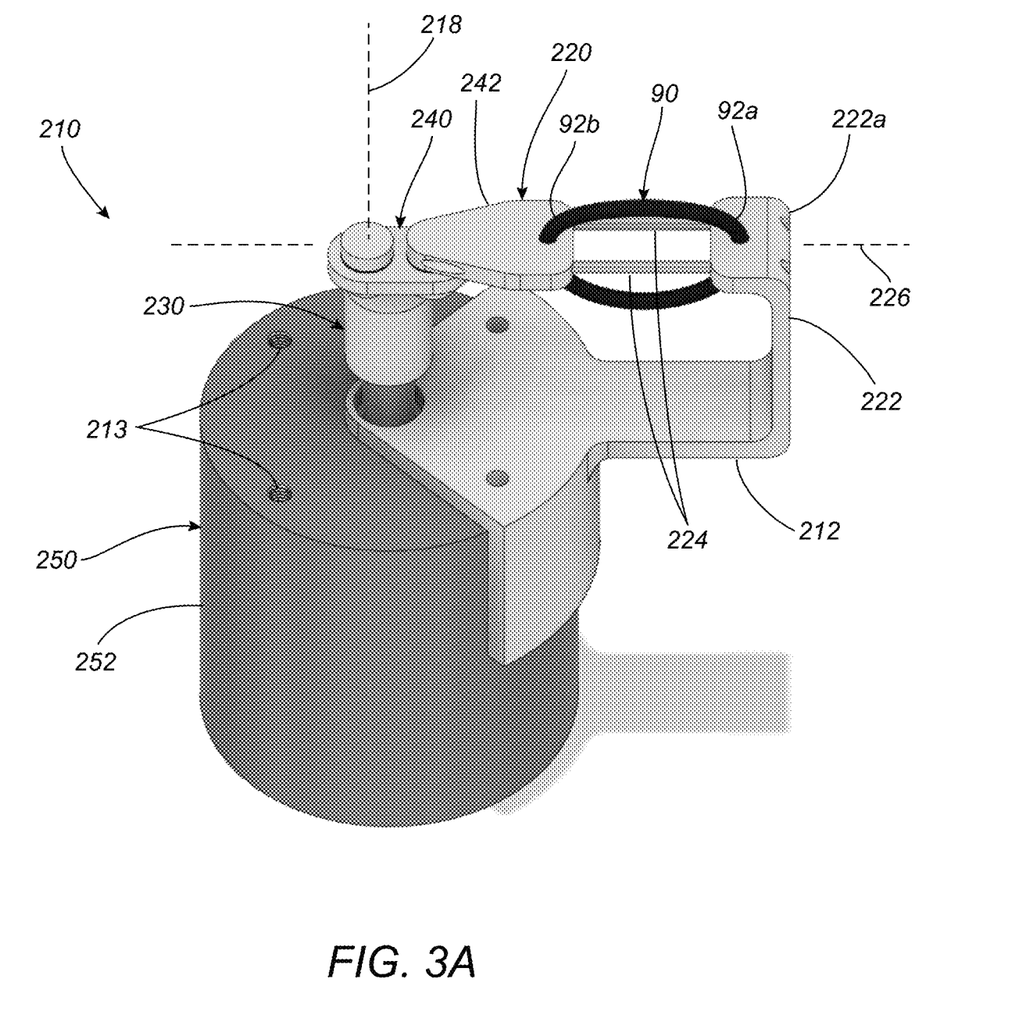
FIGS. 3A and 3B are perspective and top views, respectively, of another example of a fatigue testing device.
Figure 3B:
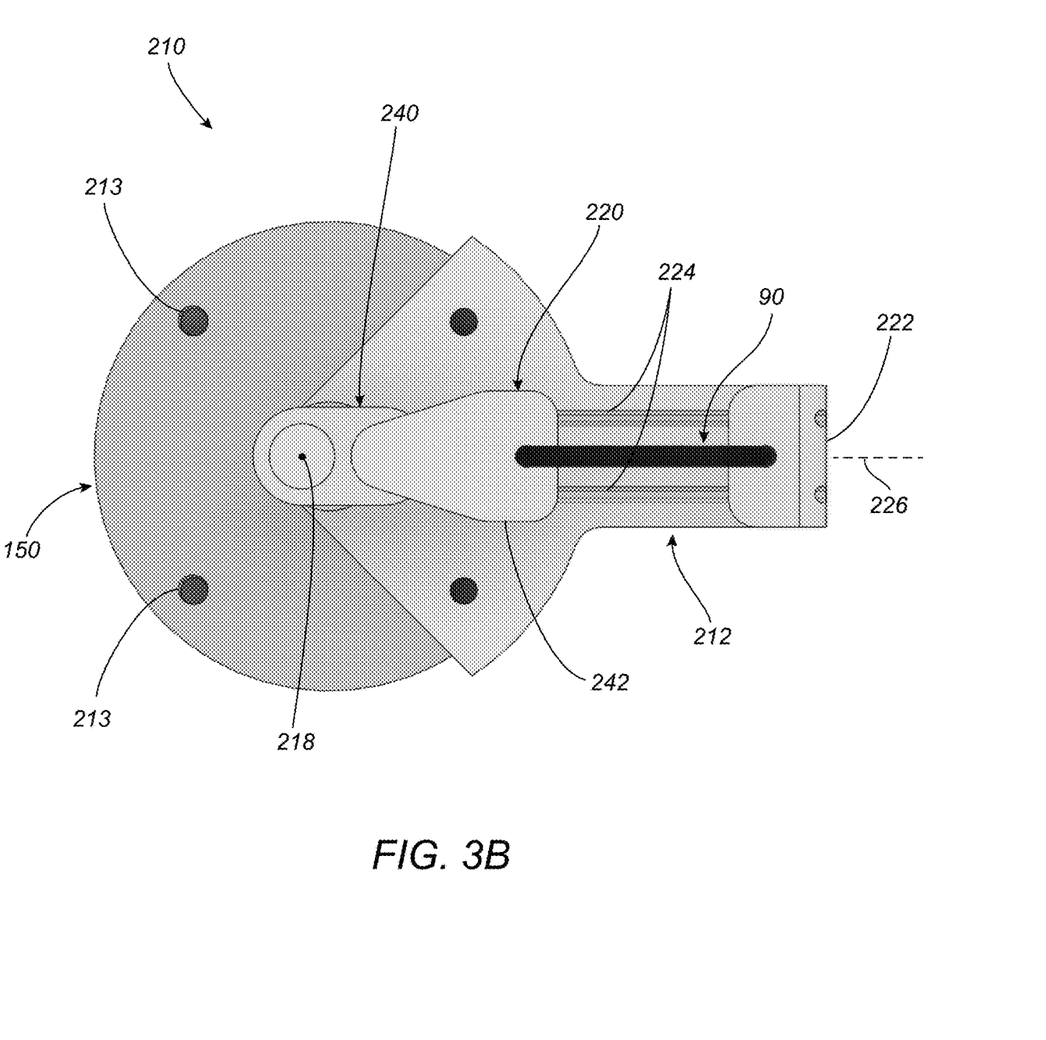

Alternatively, rather than a cam-follower arrangement, a fatigue testing device may be provided that includes other mechanisms that reciprocate one end of a device being tested relative to a stationary end. For example, as shown in FIGS. 3A and 3B, a testing device 210 is shown that uses a constrained linkage-based system, e.g., a two-bar linkage 240 connected to a linearly constrained mounting system 220. As shown, the device 210 includes a base or platform 212 mounted to or adjacent a motor 250 including a shaft 230 that rotates about a vertical axis 218, e.g., generally similar to the other devices herein.

For example, the mount 220 may include a first or stationary mount 222, e.g., a bracket including a fixed end 222a spaced from the shaft 230 and a second or sliding mount 242. A pair of rigid shafts 224 extend from the fixed end 222a substantially parallel to a horizontal axis 226, e.g., inwardly toward the shaft 230. The sliding mount 242 may be slidably mounted on the shafts 224 and the shaft 230 may be coupled to the sliding mount 242 by the linkage 240 such that the sliding mount 242 reciprocates parallel to the horizontal axis 226 as the shaft 230 rotates.

A device, e.g., an annuloplasty ring 90, may be secured to the stationary mount 222 and the sliding mount 242, respectively, to perform fatigue or other testing of the device, generally similar to the other devices herein. For example, the fixed end 222a of the stationary mount 222 may each include a connector (not shown) for removably mounting a first end 92a of the annuloplasty ring 90 to the stationary mount 222. A second end 92b of the annuloplasty ring 90 may be removably mounted by a connector (also not shown) to the sliding mount 242 coupled to the linkage 240. During testing, the linkage 240 may translate the sliding mount 242 linearly, i.e., along the horizontal axis 226, as the shaft 230 rotates about the vertical axis 218, thereby moving the second end 92b away from and towards the first end 92a, e.g., similar to the other devices herein.

These linkage systems may be actuated about any of the three spatial axes with the linear motion occurring in any axis. Such a mechanism may include a Scotch yoke, eccentric linkage, or other mechanism operatively coupling a flywheel to a piston, all of which generate a translation of rotary motion to linear motion to reciprocate one end of the device being tested.

The platform 212 may be permanently mounted to the housing 252 of the motor 250 or, alternatively, may be removable. For example, the housing 252 may include one or more pairs of holes 213 (two shown) that may be used to removably secure respective platforms 212 or mounts 212 to the housing 252, whereupon the sliding mount 224 may be coupled to the linkage 240 to perform a fatigue test, similar to the other devices described herein.

In describing representative examples, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for performing fatigue testing, the device comprising:
    a support platform;
    a cam rotatably mounted relative to a central region of the support platform such that the cam rotates about a first axis; and
    one or more sets of mounts on the support platform, each set of mounts comprising:
        a first mount;
        a second mount adjacent the central region such that the first and second mounts are aligned along a second axis orthogonal to and intersecting the first axis; and
        a follower slidably mounted to the second mount such that a first end of the follower contacts the cam such that the follower reciprocates along the second axis as the cam rotates about the first axis, and
        wherein the follower and first mount are configured to secure first and second ends, respectively, of the device being tested such that rotation of the cam causes the follower to reciprocate and direct the first end of the device being tested away from and towards the second end,
        wherein the second mount comprises one or more guide shafts extending from the first mount towards the central region along the second axis.

2. The device of claim 1, further comprising a motor mounted adjacent the platform and wherein the cam is mounted on a rotatable axle of the motor.

3. The device of claim 2, wherein the platform includes an aperture at the central region and wherein the motor is mounted below the platform such that the axle of the motor extends through the aperture.

4. The device of claim 1, wherein the cam comprises a noncircular side surface that rotates around the first axis as the cam rotates, the side surface defining a major axis and a minor axis smaller than and orthogonal to the major axis and wherein the first end of the follower contacts the side surface.

5. The device of claim 4, wherein the follower is biased to an inward position where the first end of the follower is spaced from the first axis by a distance less than half the major axis such that the cam directs the follower to an outward position when the major axis is aligned with the second axis as the cam rotates and the follower automatically returns towards the inward position when the minor axis is aligned with the second axis.

6. The device of claim 5, further comprising a spring mechanism for biasing the follower to the inward position.

7. The device of claim 1, wherein the platform comprises a plurality of sets of mounts arranged concentrically around the central region, each set of mounts including a first mount and a follower slidably mounted to a second mount aligned along respective second axes such that each follower reciprocates along the respective second axis as the cam rotates about the first axis.

8. The device of claim 7, wherein each of the sets of mounts is secured on an upper surface of the platform concentrically around the central region.

9. The device of claim 1, wherein the follower is removable from the second mount.

10. A device for performing fatigue testing, the device comprising:
- a support platform comprising an upper surface, a vertical axis extending substantially perpendicular to the upper surface at a central region, and a set of mounts on the upper surface including a first mount on the upper surface, a second mount on the upper surface adjacent the central region such that the first and second mounts are aligned along a horizontal axis orthogonal to and intersecting the first axis, and a follower slidably mounted to the second mount such that follower is slidable along the horizontal axis; and
- a cam rotatably mounted above the upper surface and aligned with the vertical axis such a first end of each follower contacts the cam and causes the follower to reciprocate along the horizontal axis as the cam rotates,
- wherein the follower and first mount are configured to secure first and second ends, respectively, of the device being tested such that rotation of the cam causes the follower to reciprocate and direct the first end of the device being tested away from and towards the second end,
- wherein the second mount comprises one or more guide shafts extending from the first mount towards the central region along the horizontal axis.

11. The device of claim 10, further comprising a motor mounted adjacent the platform and wherein the cam is mounted on a rotatable axle of the motor.

12. The device of claim 11, wherein the platform includes an aperture at the central region and wherein the motor is mounted below the platform such that the axle of the motor extends through the aperture.

13. The device of claim 10, wherein the cam comprises a noncircular side surface that rotates around the vertical axis as the cam rotates, the side surface defining a major axis and a minor axis smaller than and orthogonal to the major axis and wherein the first end of each follower contacts the side surface.

14. The device of claim 13, wherein the follower is biased to an inward position where the first end is spaced from the vertical axis by a distance less than half the major axis such that the cam directs the follower to an outward position when the major axis is aligned with the second axis as the cam rotates and the follower automatically returns towards the inward position when the minor axis is aligned with the horizontal axis.

15. The device of claim 14, further comprising a spring mechanism for biasing the follower to the inward position.

16. The device of claim 10, wherein the platform comprises a plurality of sets of mounts arranged concentrically around the central region, each set of mounts including a first mount and a follower slidably mounted to a second mount aligned along respective horizontal axes such that each follower reciprocates along the respective horizontal axis as the cam rotates.

17. The device of claim 10, wherein the follower is removable from the second mount.

* * * * *